(12) United States Patent
Hsieh et al.

(10) Patent No.: US 8,280,137 B2
(45) Date of Patent: Oct. 2, 2012

(54) SYSTEM AND METHOD OF INCREASING TEMPORAL RESOLUTION OF AN X-RAY IMAGE

(75) Inventors: Jiang Hsieh, Brookfield, WI (US);
Roy-Arnulf Helge Nilsen, Waukesha, WI (US); Peter Michael Edic, Albany, NY (US); Bruno Kristiaan Bernard De Man, Clifton Park, NY (US); Jean-Baptiste Thibault, Milwaukee, WI (US); Baojun Li, Sharon, MA (US); John Lawrence Seamans, Ann Arbor, MI (US)

(73) Assignee: General Electric Company, Schenectady, NY (US)

( * ) Notice: Subject to any disclaimer, the term of this patent is extended or adjusted under 35 U.S.C. 154(b) by 346 days.

(21) Appl. No.: 12/638,723

(22) Filed: Dec. 15, 2009

(65) Prior Publication Data

US 2011/0142314 A1    Jun. 16, 2011

(51) Int. Cl.
*G06K 9/00* (2006.01)
*G06K 9/46* (2006.01)
*A61B 6/00* (2006.01)
(52) U.S. Cl. ............. 382/131; 382/128; 382/195; 378/4
(58) Field of Classification Search .................. 382/128, 382/130, 131, 132, 168, 190, 206, 219, 254, 382/263, 305, 195; 378/4–20, 101, 109–112, 378/114, 115, 901
See application file for complete search history.

(56) References Cited

U.S. PATENT DOCUMENTS

| | | | |
|---|---|---|---|
| 7,054,475 B2 * | 5/2006 | Edic et al. | 382/131 |
| 7,221,728 B2 | 5/2007 | Edic et al. | |
| 7,778,381 B2 * | 8/2010 | Nishide et al. | 378/4 |

FOREIGN PATENT DOCUMENTS

WO    2008047268 A1    4/2008

OTHER PUBLICATIONS

Nett et al., "Temporally Targeted Imaging Method Applied to ECG-Gated Computed Tomography: Preliminary Phantom and In Vivo Experience," Academic Radiology, vol. 15, No. 1, Jan. 2008, pp. 93-106.

(Continued)

*Primary Examiner* — Sheela Chawan
(74) *Attorney, Agent, or Firm* — Ziolkowski Patent Solutions Group, SC (57) ABSTRACT

A system, method, and apparatus includes a computed tomography (CT) system having a rotatable gantry, an x-ray source, a generator, a detector having pixels and positioned to receive x-rays, and a computer. The computer is programmed to acquire CT data representative of an object, determine a first subset of the CT data, determine a second subset of the CT data, and determine a difference between the first and second subsets of the CT data to identify a motion region in the object. The computer is also programmed to update image data reconstructed from a first portion of the first subset of the CT data and corresponding to the region and reconstruct an image based on the updated image data and non-updated image data. The non-updated image data is reconstructed from a second portion the first subset of the CT data.

25 Claims, 5 Drawing Sheets

OTHER PUBLICATIONS

Qiao et al., "Region of interest motion compensation for PET image reconstruction," Physics in Medicine and Biology, vol. 52, 2007, pp. 2675-2689.

Schretter et al., "Local correction of non-periodic motion in computed tomography," Proceedings of SPIE, vol. 7258, Jan. 1, 2009, pp. 1-12.

Linney et al., "Organ Motion Detection in CT Images Using Opposite Rays in Fan-Beam Projection Systems," IEEE Transactions on Medical Imaging, vol. 20, No. 11, Nov. 2001, pp. 1109-1122.

Chen et al., "Temporal resolution improvement using PICCS in MDCT cardiac imaging," Medical Physics, vol. 36, No. 6, Jun. 2009, pp. 2130-2135.

\* cited by examiner

SYSTEM AND METHOD OF INCREASING TEMPORAL RESOLUTION OF AN X-RAY IMAGE

BACKGROUND OF THE INVENTION

Embodiments of the invention relate generally to diagnostic imaging and, more particularly, to an apparatus and method of increasing temporal resolution of an x-ray image.

Typically, in x-ray systems, such as a computed tomography (CT) imaging systems, an x-ray source emits a fan-shaped or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces an electrical signal indicative of the attenuated beam received by each detector element. The electrical signals are transmitted to a data processing system for analysis, which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy and discharges the light energy to a photodiode adjacent thereto. Each photodiode detects the light energy and generates a corresponding electrical signal. The outputs of the photodiodes are digitized and then transmitted to the data processing system for image reconstruction.

CT imaging encompasses multiple modalities. For example, one modality includes multi-slice CT imaging, which is often employed for cardiac imaging. Due to the motion of the heart, however, multi-slice CT imaging can suffer from blurring (i.e., poor temporal resolution). One technique that has been employed to minimize blurring includes increasing gantry speed to decrease overall acquisition time. By decreasing CT acquisition time, blurring may be reduced since acquisition occurs over a smaller time period. Generally, however, the weight of a gantry and other forces acting on the gantry limit the speed at which the gantry can operate. Additionally, a reduction in the acquisition time often requires more powerful x-ray tubes to achieve the same image quality.

Another technique to minimize blurring due to motion includes a two-tube-two-detector approach. In such an approach or technique, two tubes operate simultaneously, thus decreasing overall acquisition time. As such, blurring due to motion can be minimized. The cost, however, of two-tube-two-detector CT systems can be prohibitive.

It would therefore be beneficial to design a cost effective system and method that minimizes motion blurring in CT imaging.

BRIEF DESCRIPTION OF THE INVENTION

Embodiments of the invention are directed to a method and apparatus for increasing temporal resolution of an x-ray image.

According to an aspect of the invention, a computed tomography (CT) system includes a rotatable gantry having an opening for receiving an object to be scanned, an x-ray source coupled to the gantry and configured to project x-rays through the opening, a generator configured to energize the x-ray source to generate the x-rays, a detector having pixels and attached to the gantry and positioned to receive the x-rays, and a computer. The computer is programmed to acquire CT data representative of an object, determine a first subset of the CT data, determine a second subset of the CT data, and determine a difference between the first and second subsets of the CT data to identify a region in the object. The region represents motion within the object during acquisition of the CT data. The computer is also programmed to update image data reconstructed from a first portion of the first subset of the CT data and corresponding to the region and reconstruct an image based on the updated image data and non-updated image data. The non-updated image data is reconstructed from a second portion the first subset of the CT data.

According to another aspect of the invention, a method of reconstructing a computed tomography (CT) image includes acquiring CT data representative of an object, identifying a first subset of the CT data, identifying a second subset of the CT data, and locating a region within the object representative of motion within the object, where locating a region is based on a difference between the first and second subsets of the CT data. The method also includes iteratively updating image data corresponding to a portion of the first subset of the CT data and corresponding to the region and reconstructing a CT image based on the iteratively updated image data and non-iteratively updated image data.

According to yet another aspect of the invention, a tangible computer readable storage medium having stored thereon a computer program including instructions, which, when executed by a computer, cause the computer to acquire computed tomography (CT) data that represents an object, where the CT data is acquired over a first period of time via a first set of projections. The computer is also caused to identify image data corresponding to a first subset of the CT data that represents a region within the object that moved during the first period of time, update the identified image data, and reconstruct a CT image based on non-updated image data and the updated image data.

According to yet another aspect of the invention, a computed tomography (CT) system includes a rotatable gantry having an opening for receiving an object to be scanned, an x-ray source coupled to the gantry and configured to project x-rays through the opening, a generator configured to energize the x-ray source to generate the x-rays, a detector having pixels therein, where the detector is attached to the gantry and positioned to receive the x-rays, and a computer. The computer is programmed to acquire CT data representative of an object, determine a first subset of the CT data, determine a second subset of the CT data, iteratively reconstruct a first and second image based on the first and second subsets, respectively. The computer is also programmed to minimize a difference between the first and second images as the first and second images are iteratively reconstructed.

These and other advantages and features will be more readily understood from the following detailed description of preferred embodiments of the invention that is provided in connection with the accompanying drawings.

DETAILED DESCRIPTION

Embodiments of the invention support the acquisition of both anatomical detail for medical CT as well as structural detail for components within objects such as luggage.

The operating environment of the invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
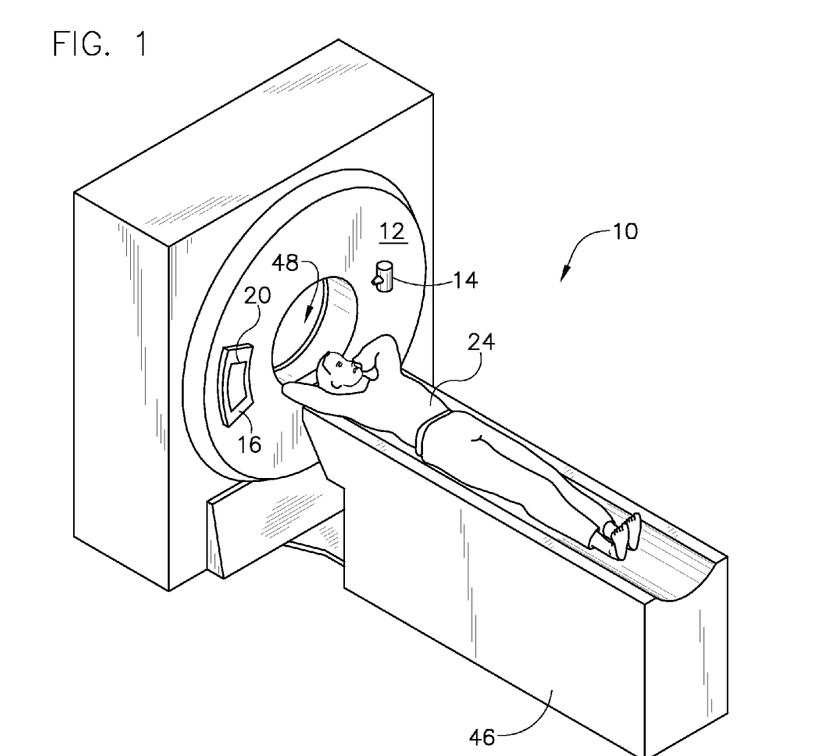
FIG. 1 is a pictorial view of a CT imaging system.
Figure 2:
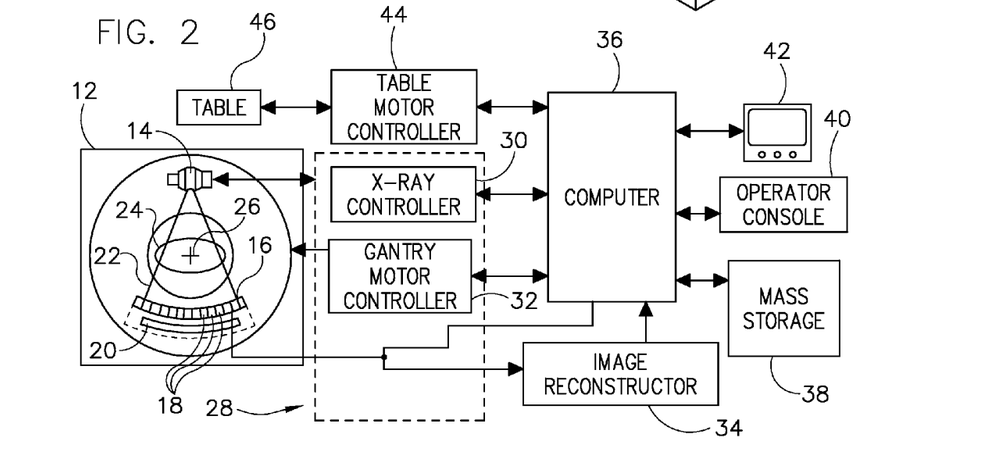
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays toward a detector assembly or collimator 16 on the opposite side of the gantry 12. Referring now to FIG. 2, detector assembly 16 is formed by a plurality of detectors 18 and a data acquisition system (DAS) 20. The plurality of detectors 18 sense the projected x-rays 22 that pass through a medical patient 24, and DAS 20 converts the data to digital signals for subsequent processing. Each detector 18 produces an analog electrical signal that represents the intensity of an impinging x-ray beam and hence the attenuated beam as it passes through the patient 24. During a scan to acquire x-ray projection data, gantry 12 and the components mounted thereon rotate about a center of rotation 26.

Rotation of gantry 12 and the operation of x-ray source 14 are governed by a control mechanism 28 of CT system 10. Control mechanism 28 includes an x-ray controller 30 that provides power and timing signals to an x-ray source 14 and a gantry motor controller 32 that controls the rotational speed and position of gantry 12. An image reconstructor 34 receives sampled and digitized x-ray data from DAS 20 and performs high speed reconstruction. The reconstructed image is applied as an input to a computer 36 which stores the image in a mass storage device 38. Image reconstructor 34, which may contain special hardware and/or software, and computer 36 may be separate hardware devices or may comprise a single device.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 20, x-ray controller 30 and gantry motor controller 32. In addition, computer 36 operates a table motor controller 44 which controls a motorized table 46 to position patient 24 and gantry 12. Particularly, table 46 moves patients 24 through a gantry opening 48 of FIG. 1 in whole or in part.

Figure 3:
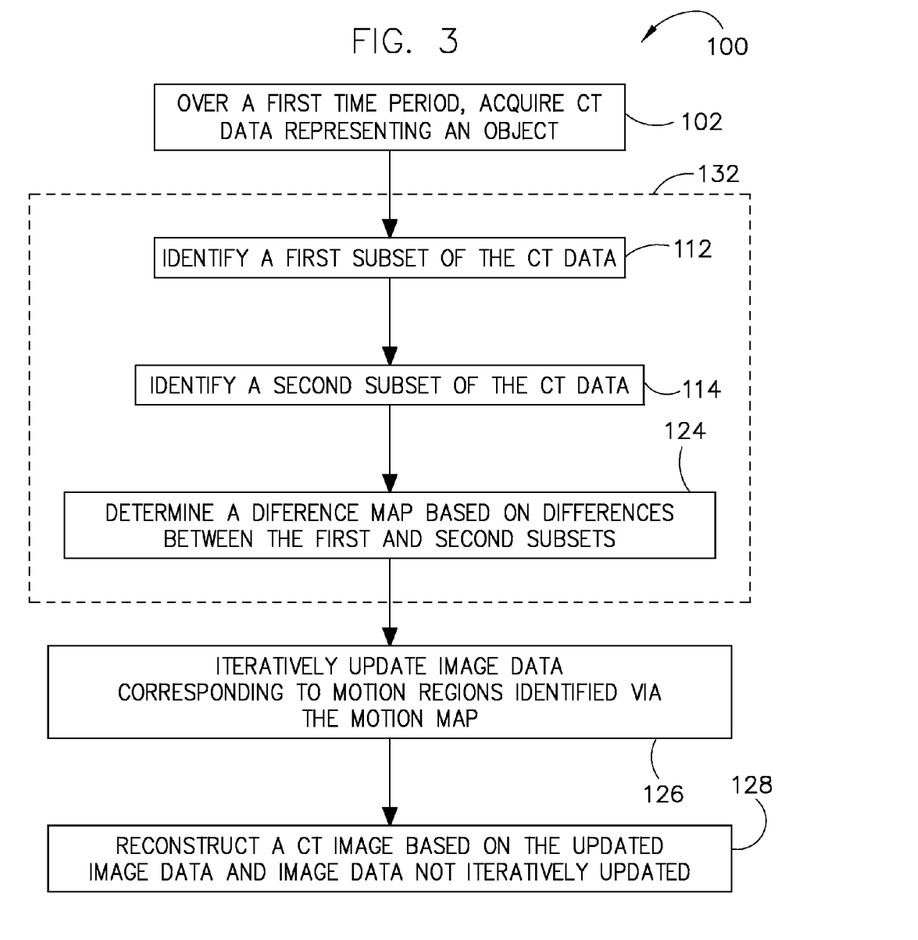
FIG. 3 is a flowchart depicting a technique for increasing temporal resolution of a CT image according to an embodiment of the invention.

Referring now to FIG. 3, a flowchart depicts a technique 100 for minimizing motion artifacts in a CT image, thus increasing temporal resolution, according to an embodiment of the invention. Technique 100 begins at block 102, where CT data representing an object is acquired over a period of time. For example, referring to FIG. 4, a line 104 represents a time period 106 over which a CT data set is acquired. Time period 106 proceeds from a scan start time 108 to a scan stop time 110. It is contemplated that the CT data acquired over time period 106 includes approximately one half-scan or more worth of projections. A half-scan acquisition, as understood by those skilled in the art, includes a quantity of projections generally equivalent to $\pi$ plus the projection fan angle. A half-scan acquisition is often considered to be the minimum number of projections needed to produce an adequate image. However, hereinafter, the phrase "half-scan acquisition" refers to a data acquisition containing either more, equal to, or less than a theoretical minimum number of projections needed to produce an adequate image.

Referring back to FIG. 3, after acquisition of the CT data, process control proceeds to block 112, where a first subset of the CT data is identified. It is contemplated that approximately one half-scan or more worth of data is represented in the first subset of the CT data. Proceeding to block 114, a second subset of the CT data is identified. Similar to the first subset of the CT data, it is contemplated that approximately one half-scan or more worth of data is represented in the second subset of the CT data.

For example, referring again to FIG. 4, according to one embodiment, a first half-scan acquisition includes a first subset of CT data acquired from start time 108 or slightly before or after the start time 108 to a first half-scan end time 116, whereas a second half-scan acquisition includes a second subset of CT data acquired from a second half-scan start time 118 to stop time 110 or slightly before or after stop time 110. The portion of time period 106 ranging from start time 108 to first half-scan end time 116 can be referred to as a first subset time period 120 of time period 106, and the portion of time period 106 ranging from second half-scan start time 118 to stop time 110 can be referred to as a second subset time period 122 of time period 106.

Figure 4:
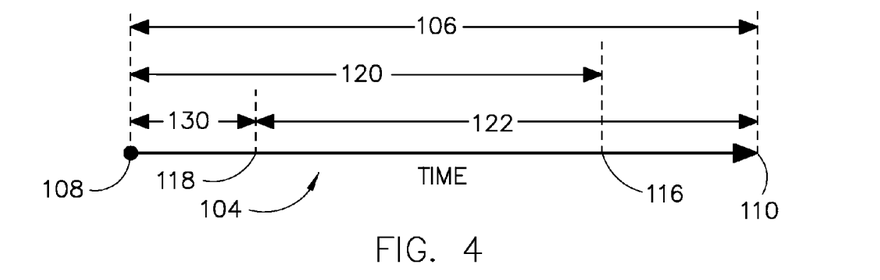
FIG. 4 is an exemplary time line depicting exemplary time periods associated with the technique of FIG. 3 according to an embodiment of the invention.

Accordingly, the first subset of CT data includes CT data that was acquired over first subset time period 120; whereas the second subset of the CT data includes CT data that was acquired over second subset time period 122. As depicted in FIG. 4, first subset time period 120 overlaps a portion of second subset time period 122. As such, the first subset of CT data shares some common data with the second subset of CT data. It is contemplated, however, that this need not be the case. That is, it is contemplated first subset time period 120 and second subset time period 122 do not share common acquisitions in one embodiment. Though not shown, in such an embodiment, a first subset time period would not overlap a second subset time period.

Referring back to FIG. 3, after the second subset of the CT data is identified, process control proceeds to block 124, where a difference image or map is determined. The difference map identifies or locates one or more regions of motion within the object based on difference(s) between the first and second subsets of the CT data. Such differences may be determined in image space or projection space. For example, according to one embodiment of the invention employed in image space, a difference between a first image based on the first subset of the CT data and a second image based on the second subset of the CT data is determined. As a result, a difference or motion map is determined. The locations of non-zero values, or substantially non-zero values, in the motion map correspond to locations within the first and second images where object motion occurred during acquisition of the CT data. Conversely, the locations of zero values, or substantially zero values, correspond to location(s) in the first and second images where the object was static, or at least substantially static, during acquisition of the CT data.

Alternatively, according to another embodiment employed in projection space, differences between the first and second subsets of the CT data are determined in projections space. However, as with a motion map determined in image space, the differences determined in projection space also results in a motion map (i.e., a projection-domain motion map) where one or more regions of motion caused by a region within the object are identified or located. This projection-domain motion map can be referred back to the image domain (i.e., a difference image map) by, for example, performing a combination of backprojection and thresholding operations.

Still referring to FIG. 3, after producing or determining the motion map, which depicts locations of motion within one or more regions of the object, process control proceeds to block 126, where image data that corresponds to the locations or regions of motion previously identified is iteratively updated via an iterative reconstruction technique. The image data corresponds to a first portion of the first subset of the CT data. As such, image data corresponding to a first portion of the first subset of the CT data, which corresponds to the locations of the one or more non-zero difference values, are updated via an iterative reconstruction technique.

It is noted that not all image data corresponding to the first subset of the CT data is iteratively updated. In other words, only image data that corresponds to the object motion located on the motion map is iteratively updated. Since all of the image data corresponding to the first subset is not iteratively updated, image updating occurs in a more efficient manner. After updating a portion of the image data, process control proceeds to block 128, where a CT image is reconstructed from the iteratively updated image data and non-iteratively updated image data, where the non-iteratively updated image data corresponds to a second portion of the CT data of the first subset. It is noted that image voxels that are outside of the identified motion location(s) can be reconstructed using more than a half-scan of acquisitions, since motion effects are not as detrimental in such location(s).

Accordingly, as set forth in technique 100, CT image data that corresponds to locations in the object that suffered from motion effects are iteratively updated, whereas the CT image data corresponding to regions outside the located motion areas are not subjected to an iterative reconstruction technique. Since the iteratively updated regions are isolated to only a portion of the image data corresponding to the first subset of the CT data set, fewer views can be used to formulate the final CT image. That is, only a portion of the image data corresponding to the first subset of the CT data set is used in the update process. As a result, image processing time is reduced since all of the image data corresponding to the first subset of the CT data was not subjected to an iterative reconstruction technique. Further, the resulting CT image has an increased temporal resolution relative to an image based on only un-updated image data since motion effects were removed or reduced. For example, if only one-half of the projection views are used to produce the final image, the temporal resolution can be improved by a factor of two.

It is noted that, instead of or in addition to updating image data corresponding to a first portion of the first subset of the CT data, image data corresponding a portion of the second subset of the CT data that corresponds to the locations identified via the motion map can be updated via an iterative reconstruction technique. In such an embodiment, the CT image having the increased temporal resolution would be reconstructed from the updated portion(s) of the image data corresponding to the second subset and the un-updated portion(s) of the image data corresponding to the second subset.

It is also contemplated that to further enhance the motion map created at block 124, high-pass filtering can be applied to first and/or second subsets of CT data in a direction parallel to a ray connecting the location of the source at the center-view and the iso-center. Accordingly, the high-pass filtering may reduce selection of undesirable pixels and/or allow a threshold to be reduced in order to allow pixels near small moving structures, such as coronaries, to be selected.

Embodiments of technique 100 may, for example, be implemented to reduce motion artifacts often present in a cardiac image. That is, a motion map may be determined to identify regions of motion in a cardiac region. For example, referring back to FIG. 4, it is contemplated that projection views acquired over first subset time period 120 may approximately correlate to a cardiac phase, whereas projection view acquired over second subset time period 122 may correlate with a different cardiac phase. Accordingly, technique 100 of FIG. 3 may be implemented to reduce cardiac artifacts that are often present in a cardiac image.

It is noted that the areas of motion detected by technique 100 may be dependent on a temporal offset between the two sets of projection views (i.e., the temporal offset between the first and second subsets of the CT data) used to generate the motion map. For example, referring again to FIG. 4, a temporal offset 130 between the projection views acquired over first subset time period 120 and second subset time period 122 may affect the magnitude of the non-zero values identified in the motion map as well as affecting the quantity of non-zero locations present in the motion map.

It is also contemplated that the local motion estimation may be improved by combining information from multiple motion maps created from a comparison of multiple sets of projection views with different offsets. As such, it is contemplated that blocks 112-114 and 124-128 may be repeated one or more times to create additional motion maps. For instance, assume a full rotation of data is available over 0.5 seconds. Then a single half-scan image may be generated from 0.25 s worth of data. With a time offset of 50 ms (see e.g., offset 130 of FIG. 4) between the time windows (see e.g., first subset time period 120 and second subset time period 122), a total of six half-scan images and five motion maps, each depicting motion locations estimated from the temporal difference between uncorrelated projection views in each image with a particular angular focus, can be generated. The combination of the information in each motion map may provide an improved technique to estimate the sparse regions of local motion in the overall scanned object.

According to another embodiment, temporal offset 130 may be configured such that a "center view" of the projections associated with first subset time period 120 is substantially 180 degrees apart from a center view of projections associated with second subset time period 122. As such, artifacts germane to the orientation of the motion relative to the angular coverage may be suppressed, thereby providing better identification of the location(s) of motion identified in the motion map. In such an embodiment, each of the first and second subsets of CT data may be represented by a root mean square (RMS) error image, respectively, that is low passed filtered.

According to another embodiment, a weighted difference of the acquired projection data associated with the first and second subsets of the CT data may be employed to increase computational efficiency, thus increasing the rate at which the temporally resolved CT image having reduced motion artifacts can be reconstructed at block 128. In such an embodiment, a back projection process can be carried out to produce the motion map.

Figure 5:
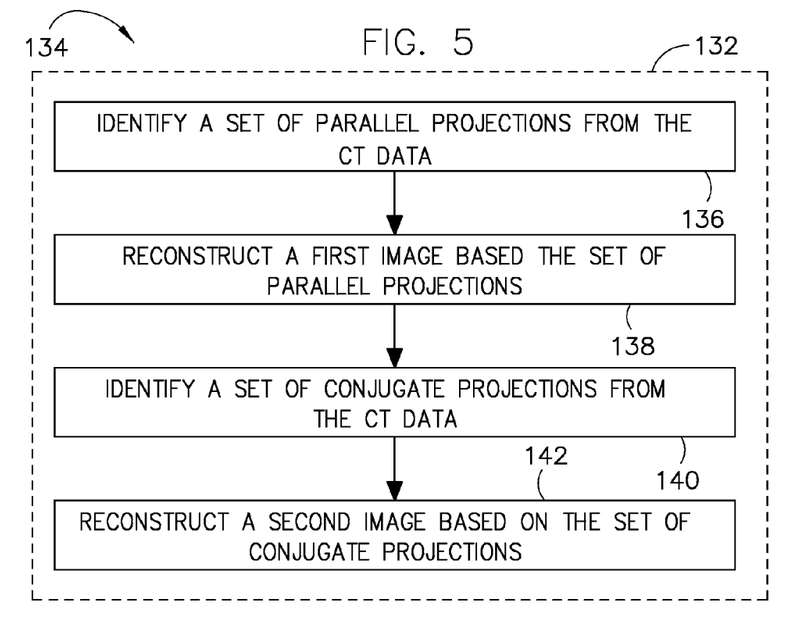
FIG. 5 is a flowchart depicting a technique for generating a motion map according to an embodiment of the invention.
Figure 6:
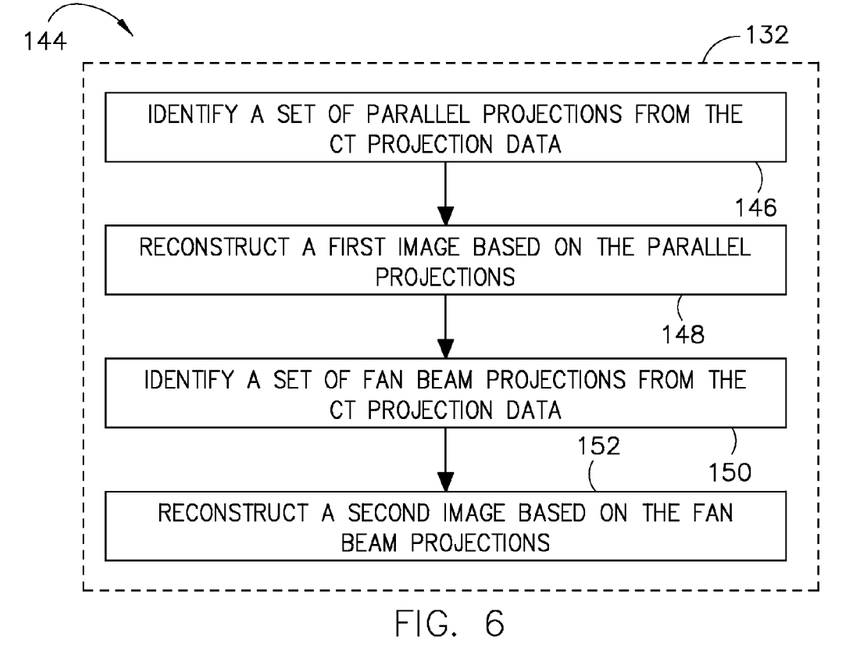
FIG. 6 is a flowchart depicting a technique for generating a motion map according to another embodiment of the invention.

Conceptually, technique 100 can be divided into four components: a) acquisition of CT data at block 102; b) generation of a motion map represented by dashed box 132, which includes blocks 112, 114, and 124; c) the iterative updating of CT data associated with the regions of motion identified via the motion map at block 126; and d) reconstruction of a temporally resolved CT image based on the updated CT data and the un-updated CT data at block 128. As discussed above with respect to block 124, a difference or motion map can be determined either in projection space or image space. Accordingly, the generation of a motion map component represented by dashed box 132 can be carried out via a variety of embodiments. FIGS. 5-6 and the accompanying description thereof depict several embodiments of motion map generation.

Referring to FIG. 5, a flowchart depicting a technique 134 for generating a motion map 132 in image space is shown according to an embodiment of the invention. Technique 134 begins at block 136, where a set of parallel projections represented in the CT data are identified, thus representing the first subset of the CT data identified at block 112 of FIG. 3. It is contemplated that a technique such as fan-to-parallel beam rebinning may be implemented to identify the parallel projections represented in the CT data. Process control then proceeds to block 138 of FIG. 5, where a first image is reconstructed from the data corresponding to the identified parallel projections (i.e., the first subset of the CT data).

After the first image is reconstructed, CT data corresponding to conjugate projections are identified at block 140 using a technique such as a fan-to-parallel rebinning technique. These conjugate projections represent the second subset of the CT data identified at block 114 of FIG. 3. Process control then proceeds to block 142 of FIG. 5, where a second image based on the data representing the conjugate projections (i.e., the second subset of the CT data) is reconstructed. As such, according to technique 134, a first image based on parallel projections is reconstructed, and a second image based on conjugate projections is reconstructed. From the first and second images, a motion map can be determined (see e.g., block 124 of FIG. 3).

Technique 134 of FIG. 5 depicts a sequence that proceeds from parallel projection data identification, to first image reconstruction based on the parallel projection data, to conjugate projection data identification, and then to reconstruction of a second image based on the conjugate projection data. It is contemplated, however, that the order in which the acts (i.e., blocks 136-142) of technique 134 are implemented may be varied. For example, reconstruction of the first image may occur after identification of the conjugate projection data or after the reconstruction of the second image.

Referring now to FIG. 6, a flowchart depicting a technique 144 for generating a motion map 132 in image space is shown according to an embodiment of the invention. Technique 144 begins at block 146, where a set of parallel projections represented in the CT data is identified, thus representing the first subset of the CT data discussed at block 112 of FIG. 3. Process control then proceeds to block 148 of FIG. 6, where a first image is reconstructed from the CT data that represents the identified parallel projections, thus reconstructing a parallel-beam CT image. It is contemplated that a view-based weighting function may be employed during such a reconstruction.

Process control then proceeds to block 150, where CT data representing fan-beam projections are identified from the CT projection data, thus representing the second subset of the CT data discussed at block 114 of FIG. 3. After identifying CT data representing fan-beam projections, a second image is reconstructed from the identified fan-beam projection CT data at block 152 of FIG. 6, thus reconstructing a fan-beam CT image. It is contemplated that a channel-and-view based weighting function may be employed during the reconstruction of the fan-beam CT image.

From the parallel-beam CT image and the fan-beam CT image, a motion map can be determined (e.g., see block 124 of FIG. 3). In such an embodiment, it is contemplated that portions of the motion map that are substantially non-zero are likely linked to the poorer temporal resolution of the parallel beam and, therefore, linked to the motion. As with technique 134 depicted in FIG. 5, it is contemplated that the order in which the acts (i.e., blocks 146-152 of FIG. 6) of technique 144 occur may be different than that shown in FIG. 6.

Still other embodiments for the determination of first and second CT images are contemplated. For example, phase and gantry motion may be manipulated such that conjugate views see little motion. In yet another embodiment, the determination of motion may be limited to one direction. For example, a determination of motion may be limited to a direction that is most susceptible to blur and artifacts, such as the direction perpendicular to the start and stop views of a half-scan. In yet another embodiment, a motion map is determined in projection space and the resulting motion map is the converted to image space.

As discussed above with respect to FIG. 3, an iterative reconstruction technique is employed to update a portion of the first or second subsets of the CT data based on region(s) of motion identified via the motion map. Generally, an iterative reconstruction technique includes a minimization of a cost function formed by the sum of a data mismatch term and regularization terms. Iteratively reconstructed data may take on the following form:

$$\hat{x} = \underset{x \in \Omega}{\operatorname{argmin}} \{F(Ax, y) + \beta U(x)\}, \quad \text{(Eqn. 1)},$$

In Eqn. 1, "y" represents the acquired projection data, "x" represents the image, "A" represents a forward projection operator in a manner similar to the scanning operation of the CT system, "F(•)" represents a distortion measure that may include different degrees of confidence between the acquired data "y" and the set "Ax" of synthesized data according to the model of the CT system, and "Ω" represents a convex set such as a set of non-negative images. Further, "βU(•)" represents a regularization term over the image "x," where "β" represents a scaling factor to balance image quality and "U(•)" represents a cost function.

A cost function, such as "U(•)", typically includes a spatial component to improve noise and spatial resolution properties of the image. For example, "U(•)" may take the form of the following:

$$U_s(x)=\Sigma_k\Sigma_j b_{jk}\phi(x_j-x_k),\quad\text{(Eqn. 2)},$$

where "$\phi(\cdot)$" represents a potential function acting on local neighbor differences, and $b_{jk}$ represents a directional scaling coefficient.

Additional information may be introduced in the iterative reconstruction process to improve temporal resolution. For example, an additional temporal regularization factor may be employed to further improve temporal resolution. An expression having an additional temporal regularization factor is shown below:

$$\hat{x}=\arg\min_{x\in\Omega\cup\Phi}\{F(Ax,y)+\beta_s U_s(x)+\beta_t U_t(x)\},\quad\text{(Eqn. 3)},$$

where $\beta_t U_t(x)$ represents the additional regularization term, $\Phi$ is the set of image voxels affected by motion according to the motion estimation, $U_s(\cdot)$ and $U_t(\cdot)$ represent cost functions, and the remaining variables generally comport with Eqn. 1. It is noted that an iterative coordinate descent approach, which performs individual voxel updates, is suited to realize such sparse updates, rather than a conjugate gradient approach or other projection based update method, which often require updating the full image at each step. Alternatively multiple voxels can be updated simultaneously using a block-based inversion technique or using a Jacobi update step.

With the knowledge of the local motion map (see e.g., block 124 of FIG. 3), voxels of the selected image (e.g., either a first image based on a first subset of the CT data or the second image based on the second subset of the CT data) can be iteratively updated only in regions where motion has been identified. As such, computational requirements are reduced by focusing computation to areas that may contain motion artifacts.

Multiple models may be employed for temporal regularization. For example, according to one model, temporal regularization is added by penalizing the difference between the most recent updated data and non-temporally-resolved data, $\tilde{x}$, that may be blurred, or include motion artifacts. In such a model, the cost function may be represented as follows:

$$U_t(x)=\Sigma_j(x_j-\tilde{x}_j)^p,\text{ with }1\leq p\leq 2\quad\text{(Eqn. 4)}.$$

where $\tilde{x}$ may be formed using a full-scan or a complete half-scan over "y," and the iterative reconstruction can be performed using less than a half-scan, where $y\subset\tilde{y}$, and using the temporal regularization to stabilize the solution. Compared to a quadratic penalty with p=2, the absolute difference function associated with p=1, and also called the L1-norm, may help localize the changes to the updated regions where motion is taking place.

Figure 7:
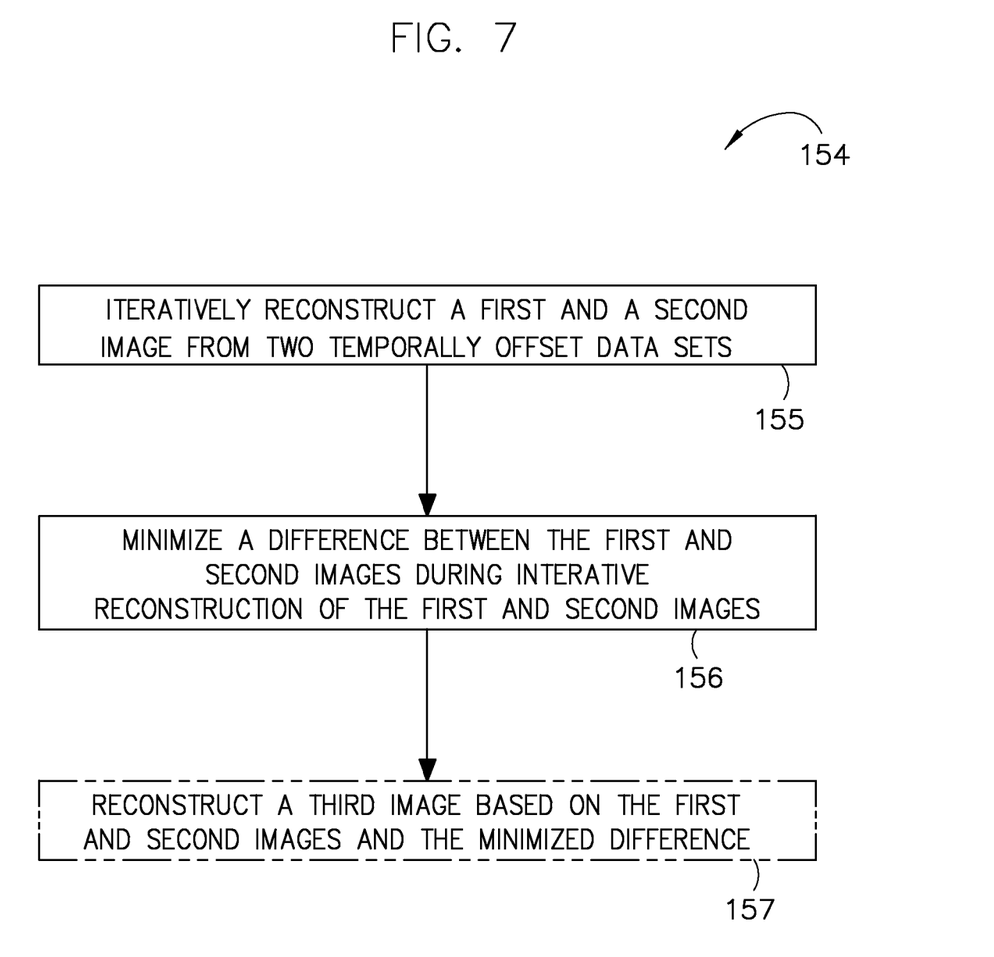
FIG. 7 is a flowchart depicting a technique for increasing temporal resolution of a CT image according to another embodiment of the invention.

In addition to the technique 100 of FIG. 3 described in detail above, alternate embodiments for increasing temporal resolution are envisioned. For example, FIG. 7 depicts a technique 154 for increasing temporal resolution according to another embodiment of the invention. Technique 154 begins at block 155 where a first image and a second image are iteratively reconstructed from temporally offset data sets (see e.g., blocks 112-114 of FIG. 3 and accompanying description where temporally offset data sets of an object are discussed). The first and second images are temporally offset and represent an object having motion therein.

As the first and second images are iteratively reconstructed, process control proceeds to block 156 of FIG. 7, where difference(s) between the first and second images are minimized during the iterative reconstruction of the first and second images. Such differences correspond to region(s) of motion within the imaged object. Accordingly, first and second time resolved images are generated. Such images may correspond to, for example, a heart during different cardiac phases.

It is contemplated that a third image may be generated, where the third image is based on, for example, a linear combination of the first and second images having the differences therebetween minimized. As such, according to an embodiment, process control proceeds to block 157, shown in phantom, where a third image is reconstructed based on the iteratively reconstructed first and second images having the differences therebetween minimized.

According to an embodiment of technique 154, an iterative reconstruction process jointly estimate two images $x^1$ and $x^2$ each from a different set of projection views (i.e., different subsets of CT data). Therefore, $x^1$ and $x^2$ have different temporal properties. An updated region therefrom can be formed as a linear combination of both $x^1$ and $x^2$, where an additional temporal regularization term penalizes large differences between $x^1$ and $x^2$ (i.e., a difference between $x^1$ and $x^2$ is minimized). The additional temporal regularization term may, for example, be presented as the cost function that follows:

$$U_t(x)=\Sigma_j(x^1_j-x^2_j)^p,\quad\text{(Eqn. 5)}.$$

Such a model can be generalized to the joint estimation of multiple images using multiple temporal sliding windows instead of only two windows. In such a generalization, the temporal regularization becomes:

$$U_t(x)=\Sigma_m\Sigma_n\Sigma_j(x^n_j-x^m_j)^p,\quad\text{(Eqn. 6)},$$

where $x^n$ are N sliding window reconstructions.

Figure 8:
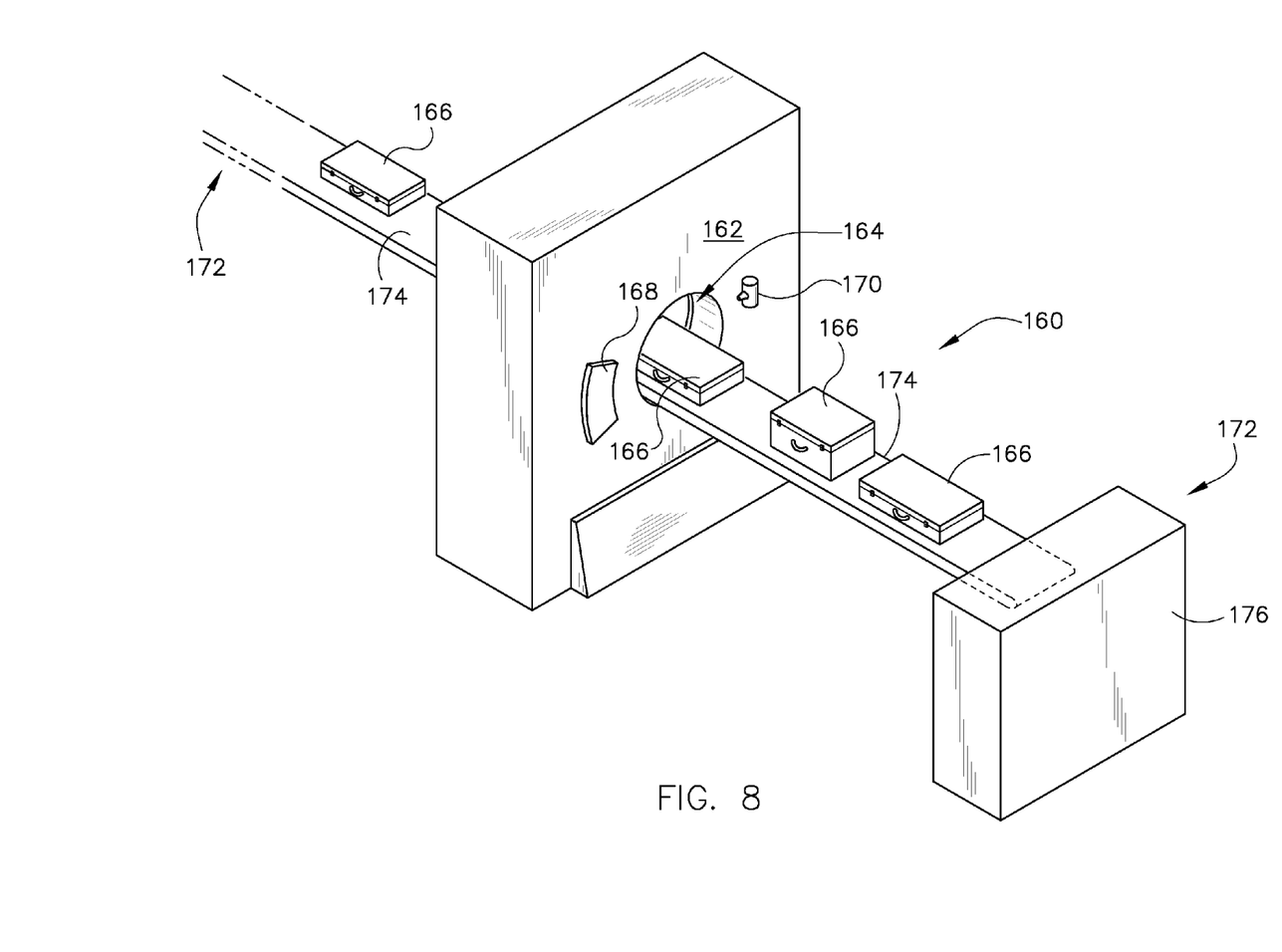
FIG. 8 is a pictorial view of a CT system for use with a non-invasive package inspection system according to an embodiment of the invention.

With respect to Eqns. 1-6 above, several iterative reconstruction techniques or models are discussed. It is, however, contemplated that other iterative reconstruction techniques not discussed may be implemented with embodiments of the invention FIG. 8 is a pictorial view of an x-ray imaging system 160 for use with a non-invasive package inspection system. The x-ray system includes 160 a gantry 162 having an opening 164 therein through which a plurality of packages or pieces of baggage 166 may pass. The gantry 162 houses a detector assembly 168 and a high frequency electromagnetic energy source, such as an x-ray tube 170. A conveyor system 172 is also provided and includes a conveyor belt 174 supported by a structure 176 to automatically and continuously pass packages or baggage pieces 166 through opening 164 to be scanned. Objects 166 are fed through opening 164 by conveyor belt 174, imaging data is then acquired, and the conveyor belt 174 removes the packages 166 from opening 164 in a controlled and continuous manner. As a result, postal inspectors, baggage handlers, and other security personnel may non-invasively inspect the contents of packages 166 for explosives, knives, guns, contraband, etc. One skilled in the art will recognize that gantry 162 may be stationary or rotatable. In the case of a rotatable gantry 162, system 160 may be configured to operate as a CT system for baggage scanning or other industrial or medical applications.

With respect to FIGS. 1 and 8, one skilled in the art will appreciate that system 10 of FIG. 1 and/or 160 of FIG. 8 includes a plurality of components such as one or more of electronic components, hardware components, and/or computer software components. These components may include one or more tangible computer readable storage media that generally stores instructions such as software, firmware and/or assembly language for performing one or more portions of one or more implementations or embodiments such as techniques 100, 134, and 144 of FIGS. 3 and 5-7, respectively. Examples of a tangible computer readable storage medium include a recordable data storage medium of the image reconstructor 34 and/or mass storage device 38 of computer 36. Such tangible computer readable storage medium may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of tangible computer readable storage media not list may be employed with embodiments of the invention.

A number of such components can be combined or divided in an implementation of the system 10 and/or 160. Further, such components may include a set and/or series of computer instructions written in or implemented with any of a number of programming languages, as will be appreciated by those skilled in the art.

According to an embodiment of the invention, a computed tomography (CT) system includes a rotatable gantry having an opening for receiving an object to be scanned, an x-ray source coupled to the gantry and configured to project x-rays through the opening, a generator configured to energize the x-ray source to generate the x-rays, a detector having pixels and attached to the gantry and positioned to receive the x-rays, and a computer. The computer is programmed to acquire CT data representative of an object, determine a first subset of the CT data, determine a second subset of the CT data, and determine a difference between the first and second subsets of the CT data to identify a region in the object. The region represents motion within the object during acquisition of the CT data. The computer is also programmed to update image data reconstructed from a first portion of the first subset of the CT data and corresponding to the region and reconstruct an image based on the updated image data and non-updated image data. The non-updated image data is reconstructed from a second portion the first subset of the CT data.

According to another embodiment of the invention, a method of reconstructing a computed tomography (CT) image includes acquiring CT data representative of an object, identifying a first subset of the CT data, identifying a second subset of the CT data, and locating a region within the object representative of motion within the object, where locating a region is based on a difference between the first and second subsets of the CT data. The method also includes iteratively updating image data corresponding to a portion of the first subset of the CT data and corresponding to the region and reconstructing a CT image based on the iteratively updated image data and non-iteratively updated image data.

According to yet another embodiment of the invention, a tangible computer readable storage medium having stored thereon a computer program including instructions, which, when executed by a computer, cause the computer to acquire computed tomography (CT) data that represents an object, where the CT data is acquired over a first period of time via a first set of projections. The computer is also caused to identify image data corresponding to a first subset of the CT data that represents a region within the object that moved during the first period of time, update the identified image data, and reconstruct a CT image based on non-updated image data and the updated image data.

According to yet another embodiment of the invention, a computed tomography (CT) system includes a rotatable gantry having an opening for receiving an object to be scanned, an x-ray source coupled to the gantry and configured to project x-rays through the opening, a generator configured to energize the x-ray source to generate the x-rays, a detector having pixels therein, where the detector is attached to the gantry and positioned to receive the x-rays, and a computer. The computer is programmed to acquire CT data representative of an object, determine a first subset of the CT data, determine a second subset of the CT data, iteratively reconstruct a first and second image based on the first and second subsets, respectively. The computer is also programmed to minimize a difference between the first and second images as the first and second images are iteratively reconstructed.

A technical contribution for the disclosed method, system, and apparatus is that it provides for a computer-implemented apparatus and method of increasing temporal resolution of an x-ray image.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Furthermore, while single energy and dual-energy techniques are discussed or implied above, the invention encompasses approaches with more than two energies. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A computed tomography (CT) system comprising:
 a rotatable gantry having an opening for receiving an object to be scanned;
 an x-ray source coupled to the gantry and configured to project x-rays through the opening;
 a generator configured to energize the x-ray source to generate the x-rays;
 a detector having pixels therein, the detector attached to the gantry and positioned to receive the x-rays; and
 a computer programmed to:
  acquire CT data representative of an object;
  determine a first subset of the CT data;
  determine a second subset of the CT data;
  determine a difference between the first and second subsets of the CT data to identify a region in the object, wherein the region represents motion within the object during acquisition of the CT data;
  update image data reconstructed from a first portion of the first subset of the CT data and corresponding to the region; and
  reconstruct an image based on the updated image data and non-updated image data, wherein the non-updated image data is reconstructed from a second portion of the first subset of the CT data.

2. The CT system of claim 1 wherein the computer is further programmed to:
 reconstruct a first image based on the first subset of the CT data; and reconstruct a second image based on the second subset of the CT data, wherein determination of a difference between the first and second subsets is based on a difference between the first and second images.

3. The computed tomography (CT) system of claim 1 wherein at least one of the first and second subsets of the CT data represents less than a half-scan acquisition.

4. The computed tomography (CT) system of claim 1 wherein the first subset of the CT data and the second subset of the CT data comprise shared data.

5. The computed tomography (CT) system of claim 1 wherein the updated image data is iteratively updated.

6. The computed tomography (CT) system of claim 5 wherein the iteratively updated image data is updated via an iterative coordinate descent approach such that no more than one voxel is updated per iteration.

7. The computed tomography (CT) system of claim 5 wherein the iteratively updated image data is updated via one of a blocked coordinate descent approach and a Jacobi method such that less than all voxels corresponding to the iteratively updated image data are updated per iteration.

8. The computed tomography (CT) system of claim 5 wherein the computer, in being programmed to iteratively update the image data, is programmed to employ a temporal regularization technique to compare a voxel with a previously updated image voxel.

9. The computed tomography (CT) system of claim 1 wherein the first subset of the CT data represents substantially a first half-scan acquisition, and wherein the second subset of the CT data represents substantially a second half-scan acquisition.

10. The computed tomography (CT) system of claim 9 wherein a center view of the first half-scan acquisition is approximately 180 degrees offset from a center view of the second half-scan acquisition.

11. The CT system of claim 1 wherein the first subset of the CT data represents a first set of projection data and the second subset of the CT data represents a second set of projection data.

12. The CT system of claim 11 wherein the first set of projection data represents parallel beam projection data and the second set of projection data represents conjugate ray projection data.

13. The CT system of claim 11 wherein the first set of projection data represents parallel-beam projection data and the second set of projection data represents fan-beam projection data.

14. A method of reconstructing a computed tomography (CT) image, the method comprising:
acquiring CT data representative of an object;
identifying a first subset of the CT data;
identifying a second subset of the CT data;
locating a region within the object representative of motion within the object, wherein locating a region is based on a difference between the first and second subsets of the CT data;
iteratively updating image data corresponding to a portion of the first subset of the CT data and corresponding to the region; and
reconstructing a CT image based on the iteratively updated image data and non-iteratively updated image data.

15. The method of claim 14 wherein a portion of the first subset of the CT data is equivalent to a portion of the second subset of the CT data.

16. The method of claim 14 further comprising:
reconstructing a first image based on the first subset of the CT data; and
reconstructing a second image based on the second subset of the CT data, wherein locating a region based on a difference between the first and second subsets of CT data is based on a difference between the first and second images.

17. The method of claim 16 further comprising applying a high pass filter to the first image prior to locating the region.

18. The method of claim 14 wherein the difference between the first and second subsets of the CT data is a difference in projection space.

19. The method of claim 14 wherein the first subset of the CT data is representative of parallel projections and the second subset of the CT data is representative of projections conjugate to the parallel projections.

20. The method of claim 14 wherein the first subset of the CT data is representative of parallel-beam projections and the second subset of the CT data is representative of fan-beam projections.

21. A non-transitory computer readable storage medium having stored thereon a computer program comprising instructions, which, when executed by a computer, cause the computer to:
acquire computed tomography (CT) data that represents an object, wherein the CT data is acquired over a first period of time via a first set of projections;
identify image data corresponding to a first subset of the CT data that represents a region within the object that moved during the first period of time;
update the identified image data; and
reconstruct a CT image based on non-updated image data and the updated image data.

22. The computer readable storage medium of claim 21 wherein the computer is further caused to:
reconstruct a first image based on a first portion of the CT data, wherein the first portion of the CT data includes the first subset of the CT data; and
reconstruct a second image based on a second portion of the CT data, wherein identification of the image data is based on a difference between the first and second images.

23. The computer readable storage medium of claim 21 wherein the computer is further caused to:
identify a first set of projections represented in the CT data set; and
identify a second set of projections represented in the CT data set, wherein identification of the image data is based on a projection space difference between the first and second sets of projections.

24. The computer readable storage medium of claim 21 wherein identification of the image data comprises:
identification of a first portion of the CT data that represents a first plurality of parallel projections that have passed through the object at first angle;
identification of a second portion of the CT data that represents a second plurality of parallel projections that have passed through the first object at a second angle approximately 180 degrees greater than or less than the first angle; and
determination of a difference value between the first plurality of parallel projections and the second plurality of parallel projections to identify the first subset of CT data.

25. A computed tomography (CT) system comprising:
a rotatable gantry having an opening for receiving an object to be scanned;
an x-ray source coupled to the gantry and configured to project x-rays through the opening;

a generator configured to energize the x-ray source to generate the x-rays;
a detector having pixels therein, the detector attached to the gantry and positioned to receive the x-rays; and
a computer programmed to:
  acquire CT data representative of an object;
  determine a first subset of the CT data;
  determine a second subset of the CT data;
  iteratively reconstruct a first and second image based on the first and second subsets, respectively; and
  minimize a difference between the first and second images as the first and second images are iteratively reconstructed.

* * * * *